United States Patent
Zhang et al.

(10) Patent No.: US 6,603,990 B2
(45) Date of Patent: Aug. 5, 2003

(54) **SEPARATION AND IDENTIFICATION OF WATER AND FAT MR IMAGES AT MID-FIELD STRENGTH WITH REDUCED $T_2/T_2^*$ WEIGHTING**

(75) Inventors: Weiguo Zhang, Foster City, CA (US); David M. Kramer, Corte Madera, CA (US)

(73) Assignee: Toshiba America MRI, Inc., Tustin, CA (US)

( * ) Notice: Subject to any disclaimer, the term of this patent is extended or adjusted under 35 U.S.C. 154(b) by 0 days.

(21) Appl. No.: 09/925,520

(22) Filed: Aug. 10, 2001

(65) Prior Publication Data

US 2003/0060697 A1 Mar. 27, 2003

(51) Int. Cl.$^7$ .............................. A61B 5/055
(52) U.S. Cl. ............... 600/410; 600/419; 382/128; 382/130; 324/307; 324/309
(58) Field of Search ............... 600/407, 410, 600/420; 382/128; 324/307, 309, 306, 312, 314, 300, 320, 311

(56) References Cited

U.S. PATENT DOCUMENTS

| | | | | |
|---|---|---|---|---|
| 4,720,679 A | * | 1/1988 | Patrick et al. | 324/309 |
| 5,602,476 A | | 2/1997 | Liu et al. | |
| 5,617,028 A | | 4/1997 | Meyer et al. | |
| 5,652,514 A | * | 7/1997 | Zhang et al. | 327/307 |
| 5,701,074 A | * | 12/1997 | Zhu | 324/307 |
| 5,909,119 A | | 6/1999 | Zhang et al. | |
| 5,995,863 A | | 11/1999 | Farace et al. | |
| 6,016,057 A | | 1/2000 | Ma | |
| 6,091,243 A | | 7/2000 | Xiang et al. | |
| 6,147,492 A | * | 11/2000 | Zhang et al. | 324/307 |
| 6,263,228 B1 | * | 7/2001 | Zhang et al. | 128/899 |

* cited by examiner

Primary Examiner—Marvin M. Lateef
Assistant Examiner—Jeoyuh Lin
(74) Attorney, Agent, or Firm—Nixon & Vanderhye P.C.

(57) ABSTRACT

A magnetic resonance imaging (MRI) method is disclosed for generating and identifying water and fat separated MR images. Image data is first acquired to obtain two echo images with the water and fat signals orthogonal in the first echo image, and parallel/anti-parallel in the second echo image. The effect of background field inhomogenities are removed, and water and fat images are separated from each other. The separated water and fat images are identified according to the difference of their precessing frequencies.

28 Claims, 6 Drawing Sheets

SEPARATION AND IDENTIFICATION OF WATER AND FAT MR IMAGES AT MID-FIELD STRENGTH WITH REDUCED $T_2/T_2^*$ WEIGHTING

FIELD OF THE INVENTION

This invention relates generally to magnetic resonance (MR) imaging (MRI) techniques. In particular, it relates to methods for generating water/fat separated images and, more particularly, to a method for generating and identifying water/fat component MR images with reduced $T_2/T_2^*$ weighting.

BACKGROUND AND SUMMARY OF THE INVENTION

In broad summary, the present invention relates to MRI techniques for generating images in which fat and water regions can be readily discerned. MRI is often used to non-invasively generate images of the internal organs and other body parts of human patients. It is desirable to distinguish regions of water and fat in an MR image of a patient. Distinguishing water and fat regions using MR imaging techniques is difficult. At mid-field strength the Three-Point Dixon method is the method of choice for separating water and fat images. The original Dixon method for separation of water and fat images depends upon the ability to accurately compensate for inhomogeneities in a polarizing static magnetic field $B_O$.

A problem in using the original Dixon method occurs because of inhomogeneities in the static $B_O$ field. Prior approaches to this problem have utilized additional information obtained during single or multiple scans (each having some associated disadvantages). One such prior approach is disclosed in U.S. Pat. No. 5,909,119 (the '119 patent) entitled "Method and Apparatus for Providing Separate Fat and Water MRI Images In A Single Acquisition Scan".

Prior approaches for separating images of water and fat have not been entirely successful in generating MR images that provide good contrast between fat and water regions. Some approaches are slow and require at least three MR scans. These approaches with long acquisition times are susceptible to motion problems that arise if the patient moves during the scan period. Approaches that use single scans (and have fast scan periods) have long minimum echo periods, which result in heavy $T_2/T_2^*$ weighted image contrasts. Heavy $T_2/T_2^*$ weighting is undesirable when strong $T_1$ weighting is desired. Some single scan approaches, such as that disclosed in the '119 patent, do not uniquely identify water and fat nuclei images after separation. Instead, user intervention relying on anatomical information is needed for the identification. Accordingly, there are long-felt needs for an MRI technique able to uniquely identify water and fat regions, and that provides water and fat images with reduced $T_2/T_2^*$ weighting. The present invention fulfills these needs.

By way of general background, MRI systems use the nuclear magnetic resonance (NMR) effects that RF transmissions at the nuclei Lamor frequency have on atomic nuclei having a net magnetic moment such as those in hydrogen. Applying RF transmissions to a patient affects the nuclear spin moments of the atomic nuclei in the body of the patient. The net magnetic moment of the nuclei in the patient are first magnetically aligned by a strong static magnetic field $B_0$ (e.g., typically created by magnetic poles on opposite sides of the MRI imaging volume or inside a solenoidal cryogenic superconducting electromagnet). The static field $B_0$ is altered by gradient magnetic fields created in the X, Y, and Z directions of the imaging volume. Selected nuclei, which are in spin alignment with the $B_0$ field, are nutated by a perpendicular magnetic field of a NMR RF transmission at the Lamor frequency. The nutation causes a population of such nuclei to tip from the direction of the magnetic field $B_0$.

Figure 1:
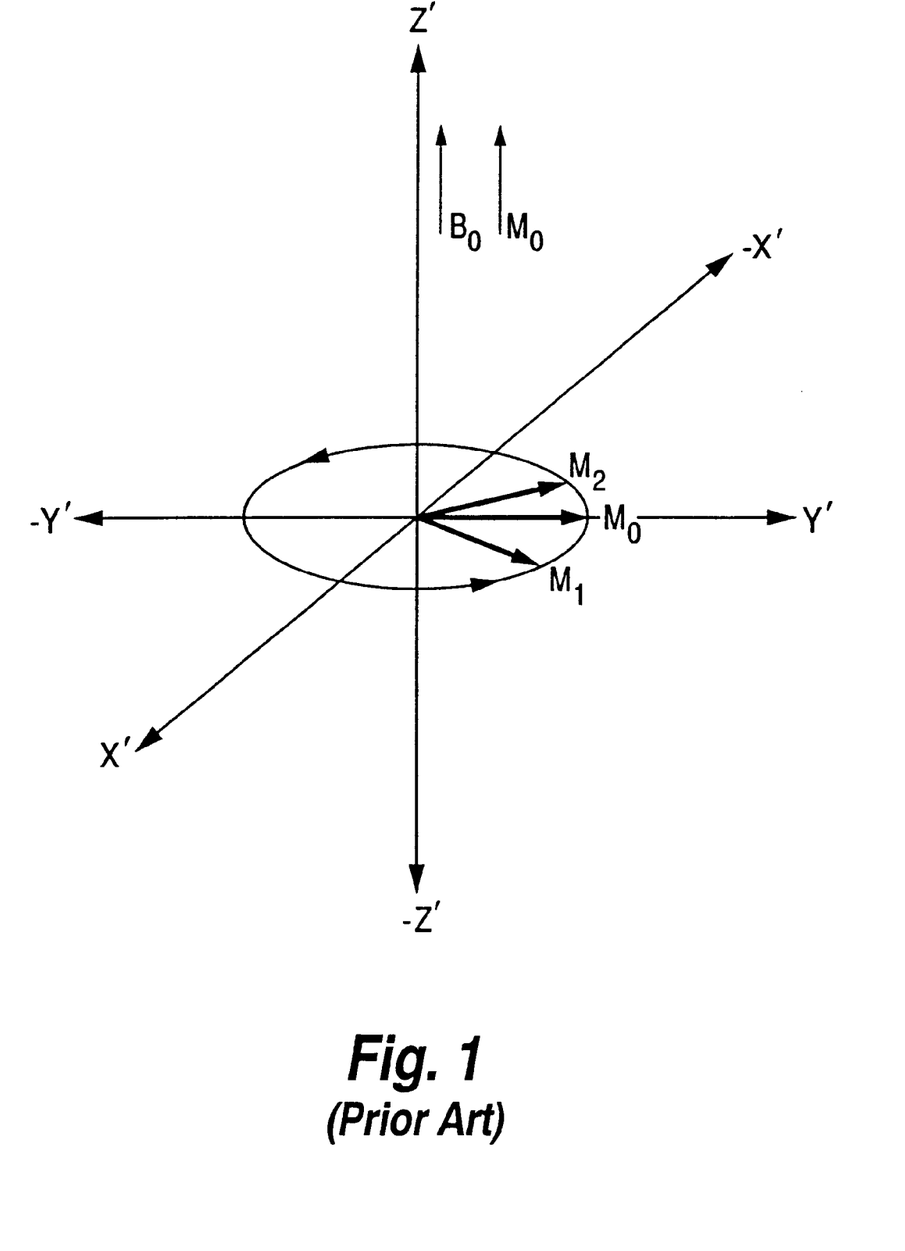
FIG. 1 is a schematic diagram of a typical rotating frame of MRI signals.

As shown in FIG. 1, certain nuclei (designated by magnetic moment $M_0$) are aligned with the "Z'" axis by the static $B_0$ field and then rotated to the X'–Y' plane as a result of an RF signal being imposed on the nuclei. The nuclei then precess in the X'–Y' plane as shown by the circulating arrow in FIG. 1 (which is a reference frame rotating at the nominal Lamor resonance frequency around the Z' axis).

The NMR RF spin-nutating signal tips more than one nuclei species in the area targeted by the RF signal. Immediately after the nutating RF signal tips the nuclei, the spinning nuclei of all species are in-phase with each other. The rotating magnetic moments of all NMR species initially all rotate across the 'Y' axis all at approximately the same time. However, after the NMR nutating RF pulse ends, each species of nuclei begin to freely precess at its own characteristic speed around the Z' axis.

As these nuclei precess, the phases of each of the rotating nuclei species will differ as a result of such parameters as the physical or chemical environment in which the nuclei are located. Nuclei in fat, for example, precess at a different rate than do nuclei in water. This difference in phase between water and fat nuclei is detected and used to distinguish water and fat in an MR image. In an MRI imaging pulse sequence there are also magnetic field gradients which dephase the moments due to their local resonance frequency varying in space. These phase differences in the nuclei spin moments are detected by an RF receiver and are used to determine the location and type of the source nuclei.

Once the nuclei spins are disturbed from their equilibrium, "relaxation" processes cause the phase-coherent component of magnetic moments in the X'–Y' plane to decay and the Z'-component to recover to its equilibrium magnitude, $M_0$. These processes are usually characterized by exponentials whose time constants are called $T_2$ and $T_1$ decay times, respectively. When magnetic resonance signals are observed through flux oscillation in a plane coexistent with the X'–Y' plane, both of these processes decrease the signal strength as a function of time.

The relative phase of components of the magnetic moments in the X'–Y' plane of FIG. 1 begin aligned on the Y'-axis, but over time they spread out and disperse to fill the full rotational area in the X'–Y' plane. The nuclei of moment $M_2$, for example, which initially crossed the Y'-axis at the same time as $M_0$, gradually moves during the dephasing period to the position shown in FIG. 1 as it spins faster than $M_0$. $M_1$, by contrast, spins slower than both $M_0$ and $M_2$, and thus begins to lag them during the dephasing period. The strength of the detectable NMR response signal decays as the relative phases of the magnetic moments disperse (i.e., lose phase coherence) in the X'–Y' plane, a process often referred to as $T_2^*$ relaxation.

Information about NMR hydrogen nuclei can be obtained, in part, by measuring their $T_2$ and $T_1$ decay times. In addition, before the nuclei become completely dephased, another RF signal (e.g., a 180° signal) can tip the magnetic moments (e.g., to a 180° inverted position). This RF signal inverts the spinning magnetic moments $M_0$, $M_1$ and $M_2$ of the three species of nuclei so the fastest moment $M_2$ now lags (instead of leading) moment $M_0$, which in turn also now lags the slowest moment $M_1$. Eventually, the faster moment $M_2$ will again catch up with and pass the slowest moment $M_1$ during which, a so-called "spin-echo" NMR RF response can be detected from the changes in net magnetic moment as the various magnetic moments come back into phase coherence. The whole procedure must be completed before $T_1$ or $T_2$ relaxation processes destroy the detectable X'–Y' components of the magnetic moments.

Detectable NMR RF response echoes can also be formed by application of a field gradient and the subsequent reversal of the gradient, provided that the reversal is done before $T_1$ or $T_2$ relaxation decays destroy $M_{X'Y'}$. This is commonly called a field echo, gradient echo or racetrack echo.

The differences in the phase relationships between the species of nuclei in one tissue versus another can be used as information to separate MRI images of fat components of tissue from fluids or water-based tissue (for these purposes, "water-based tissue" and "fluids" are used interchangeably). Although MR images of both water and fat may contain the same or different diagnostic information, they often interfere with each other's interpretation when overlapped in an MRI image and thus make it difficult to properly interpret the composite MR image. Somewhat different diagnostic information may also be obtained from separate MR images of only the fat-based or water-based species of NMR nuclei. At high field strengths, the separation of water and fat images or suppression of fat signals can be achieved using selective excitation or non-excitation approaches. However, at mid- or low-field strengths, approaches based on chemical shift selectivity become impractical, if not impossible. At all-field strengths, the difficulties of water/fat image separation are further exacerbated when there are large magnetic field inhomogeneities.

The difficulty in separating fat and water images in a practical MR imaging application is particularly true for mid- and low-field systems where the frequency separation between the water and fat signals is much reduced in comparison to that at high fields. The Three-Point-Dixon method has promising features for mid- or low field applications. It uses a single spin-echo sequence, but relies on the acquisition of three images for water/fat separation, an in-phase image and two out-phase images. A relatively-long scan period is required to acquire three images. Such long scan periods are susceptible to motion problems.

Figure 2:
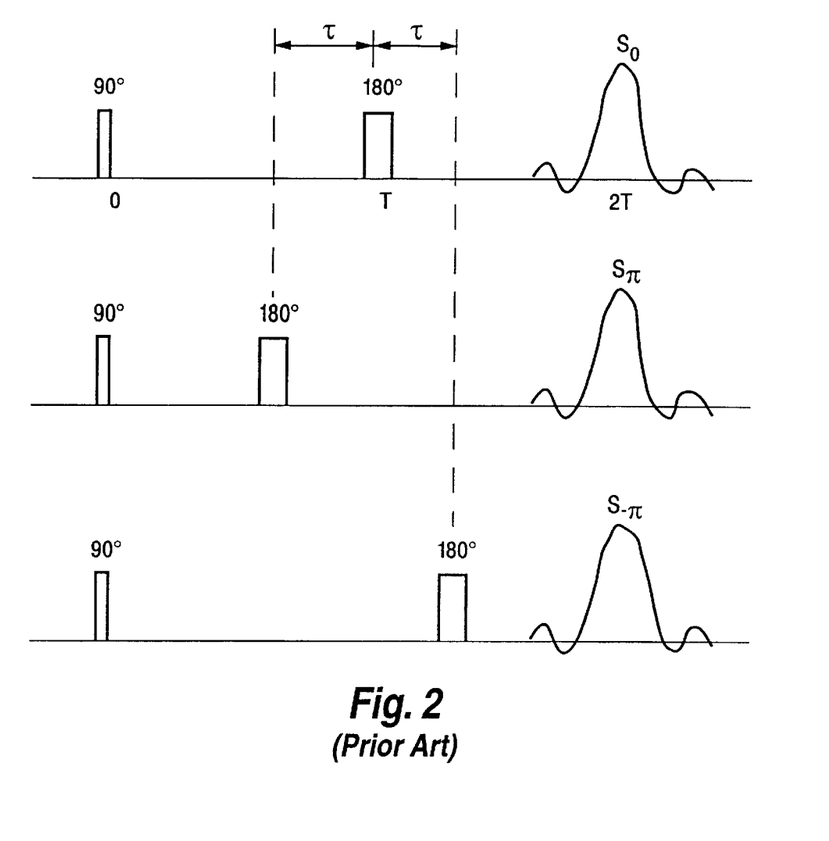
FIG. 2 is a graphical representation in the time domain of a conventional three-step Dixon MR sequencing technique.

FIG. 2 shows the three data acquisition schemes for the three images in the Three-Point Dixon method. Slice selection is not shown for simplicity. Three different scans are used to generate three spin echo signals $S_0$, $S_\pi$, $S_{-\pi}$. In the first scan, a 90° pulse is followed by a 180° pulse at a time T, yielding the spin echo $S_0$. Then, a 90° pulse is followed by a 180° pulse a time T earlier than the time T, yielding a spin echo $S_\pi$. Finally, another 90° pulse is followed by a 180° pulse a time τ later than the time T, yielding a spin echo $S_{-\pi}$. The Dixon Methodology is described in "*Three-Point Dixon Technique for True Water Fat Decompositions with $B_0$ Inhomogeneity Corrected,*" 18 Magnetic Resonance in Medicine, 371–383 (1991), by Glover et al., "*True Water and Fat MR Imaging With Use of Multiple-Echo Acquisition*", 173 Radiology 249–253 (1989), by Williams et al., "*Separation of True Fat and Water Images By Correcting Magnetic Field Inhomogeneity In Situ,*" 159 Radiology 783–786 (1986), by Yeung et al., which are incorporated herein by reference, and are summarized in part below.

Figure 3A:
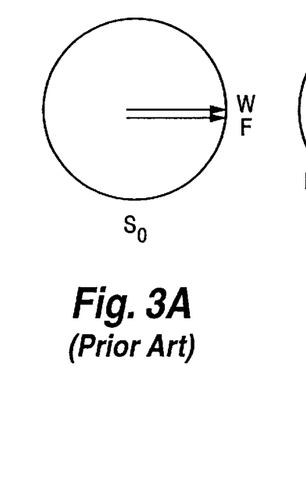
FIGS. 3A, 3B and 3C are sequence diagrams of rotating frames of the MRI signals shown in FIG. 2.
Figure 3B:
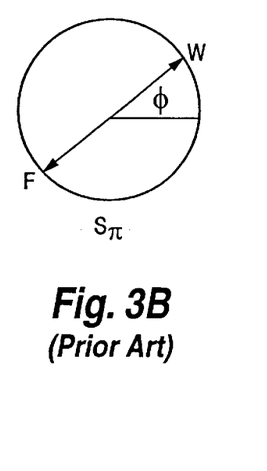
Figure 3C:
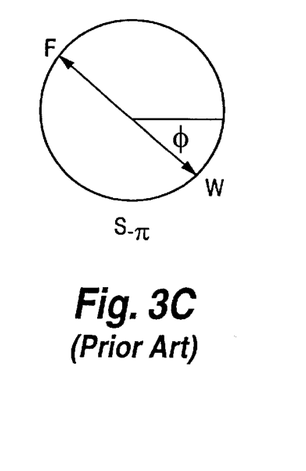

The value of τ (shown in FIG. 2) is determined according to $\tau=1/(4\Delta v)$ with $\Delta v$ being the frequency difference between the water and fat signals. The value of τ is chosen so the phase between the nuclei in, respectively, fat and water are: (1) in-phase, (2) out-of-phase by π, and (3) out-of-phase by −π. FIGS. 3a, 3b and 3c schematically show in a rotating frame the MR signals in the three different acquisition schemes. Other phase differences than π can also be used as described in Hardy et al., *JMRI*, 1995. Additionally, the So signal could be derived from a gradient reversal induced field echo. It is not required that So be an RF-induced spin echo.

In a brief summary of the three point Dixon method, three NMR RF responses are required to compute separate water-based and fat-based images:

$S_0$=a first NMR response with phase coherent fat and water NMR species;

$S_\theta$=a second NMR response with a predetermined difference between fat and water NMR species in a first (e.g., "positive") direction; and $S_{-\theta}$=a third NMR response with the same predetermined phase difference between fat and water NMR species in the opposite (e.g., "negative") direction.

Once $S_0$, $S_\theta$, $S_{-\theta}$ and θ are known, then separate MR images of the NMR fat species and/or the NMR water species can be derived.

The following is a more specific description of an exemplary embodiment of the Three-Point Dixon method in which θ=π is detailed in the Dixon paper. In the presence of field inhomogeneities, the MR signals can be described by:

$$S_0=(P_w+P_f)$$
$$S_\pi=(P_w-P_f)e^{i\phi}$$
$$S_{-\pi}=(P_w-P_f)e^{-i\phi}$$

where φ is the phase angle due to field inhomogeneities or frequency offset, and $P_w$ and $P_f$ are water and fat spin densities, respectively.

Thus, φ can be determined from $S_\pi$ and $S_{-\pi}$ by:

$$\phi=\tfrac{1}{2}arg(S_\pi \cdot S^*_{-\pi})$$

where "arg" produces the phase angle of a complex number.

Water and fat images ($I_{water}$ and $I_{fat}$, respectively) can then be reconstructed according to:

$$I_{water}=S_0+0.5S_\pi e^{-i\phi}+0.5S_{-\pi}e^{i\phi}$$
$$I_{fat}=S_0-0.5S_\pi e^{-i\phi}-0.5S_{-\pi}e^{i\phi}$$

The phase angle φ is generally determined by phase mapping. Calculating φ from $S_\pi$ and $S_{-\pi}$ involves: (1) evaluating pixel-by-pixel the principle phase value of $S_\pi \cdot S_{-\pi}^*$ to yield a principle phase map; (2) unwrapping the principle phase map to yield a true phase map.

In the past, water/fat separation at low and mid-level field intensities have been most successfully achieved using the above-discussed Three-Point Dixon methods. Moreover, as described in the '119 patent, a single-scan Three-Point Dixon method (with the water and fat signals evolving a phase difference of π during the inter-echo time (ΔTE)) can acquire three consecutive NMR echo signals after only a single excitation pulse resulting in a significant reduction in scanning-time.

The '119 patent describes a single-scan Three-Point Dixon imaging method to obtain the NMR raw signal data. In Three-Point Dixon imaging, a slice-selective excitation pulse is followed by the acquisition of three separate gradient-refocused signal-echoes. Each signal echo is acquired by controlling the timing and polarity of an applied read-out gradient. The time (ΔTE) between the signal-echoes ($S_1$, $S_2$, $S_3$) are selected according to the chemical-shift difference between water and fat signals, so that the two signals develop between them an angular difference of π radians (180°) during the inter-echo time. This 180° angular difference makes it difficult to uniquely identify fat and water images after separation, for reasons described below.

In the method described in the '119 patent, after Fourier conversion of the raw data (k-space data) to complex frequency-domain data, also called "image-domain" data, background magnetic field inhomogeneities are compensated by obtaining the compensation phase from the $S_1$ and $S_3$ signal-echoes using a guided region-growing phase unwrapping technique. The acquired image data are then corrected according to the compensation phase determined from $S_1$ and $S_3$. Water and fat signals are finally separated from the corrected image data, producing water-only or fat-only images.

The technique disclosed in the '119 patent acquires and processes echo images in which water and fat signals are either parallel or anti-parallel, which is the so-called sampling symmetry. Thus, the three echo images acquired using the approach taught in the '119 patent can be described as:

$$S_1 = (W-F)e^{-i\phi}e^{-i\Phi}$$
$$S_2 = (W+F)e^{-i\Phi}$$
$$S_3 = (W-F)e^{+i\phi}e^{-i\Phi}$$

where $\phi$ and $\Phi$ are spatial dependent phase angles, $S_1$, $S_2$ and $S_3$ are first, second and third NMR responses; and W and F are the water and fat echo images, respectively.

To correct for phase angles caused by static magnetic field $B_O$ inhomogeneities, the approach described in the '119 patent devotes a great deal of effort to determine $\phi$ from $\arg(S_3 \cdot S_1^*)$. To determine the real $\phi$ from the principle phase values, the combined phase images, $P = \arg(S_3 \cdot S_1^*)$ is phase-unwrapped using a complex seed-oriented region-growing algorithm described in the '119 patent.

In the approach described in the '119 Patent and depending on the chemical composition of the seed pixel, i.e., whether it is water-dominant (W>F) or fat-dominant (F>W), the unwrapped phase image has two possibilities:

Case 1 where W>F:

$$P = 2\phi$$
$$I_W = S_2 + \frac{1}{2}S_1 e^{i\frac{P}{2}} + \frac{1}{2}S_3 e^{-i\frac{P}{2}}$$
$$I_F = S_2 - \frac{1}{2}S_1 e^{i\frac{P}{2}} - \frac{1}{2}S_3 e^{-i\frac{P}{2}}$$

Case 2 where F>W:

$$P = 2(\phi + \pi)$$
$$I_W = S_2 - \frac{1}{2}S_1 e^{i\frac{P}{2}} - \frac{1}{2}S_3 e^{-i\frac{P}{2}}$$
$$I_F = S_2 + \frac{1}{2}S_1 e^{i\frac{P}{2}} + \frac{1}{2}S_3 e^{-i\frac{P}{2}}$$

With the approach described in the '119 patent, water and fat signals are symmetrical in that they are either parallel or anti-parallel in all echo images. Because of this Phase symmetry, information about the difference between the precessing frequencies of water and fat nuclei is lost. Moreover, there is no other information available to automatically distinguish the water and fat signals. The descriptions in the '119 Patent assumes that the seed pixel for phase unwrapping is water-dominant. Though water and fat images are separated, there needs to be other information. Such as anatomical differences that is used to correctly identify the separated water and fat images.

SUMMARY OF INVENTION

An MRI technique has been developed for distinguishing and uniquely identifying water and fat regions, and for doing so with relatively-low $T_2$ and $T_2^*$ weighting. This MRI technique breaks the sampling symmetry of prior techniques for distinguishing water and fat signals, such as is described in the '119 patent. The sampling symmetry refers to the acquisition of image data from water and fat signals that are either parallel (in-phase) or anti-parallel (180° out-of-phase) at the centers of all echo signals. To break the sampling symmetry, the present technique acquires two echo images with water and fat signals that are orthogonal (90° out-of-phase) and parallel/anti-parallel, respectively. By breaking the sampling symmetry and acquiring two echo images, the present technique is able to acquire echo signals in a shorter period of time, thus reducing $T_2$ and $T_2^*$ weighting. By acquiring an echo signal in which water and fat signals are orthogonal, water and fat images can be absolutely identified according to their difference in precessing frequencies, as described later.

In one embodiment, the invention is a method of separating and identifying water and fat magnetic resonance (MR) images using an MRI apparatus, comprising the steps of: a) obtaining nuclear magnetic resonance (NMR) image data from at least a first MR echo signal and a second MR echo signal, where water and fat signals are orthogonal in the first MR echo signal and water and fat signals are either parallel or anti-parallel in the second MR echo signal; b) obtaining a field map of background main magnetic field from the second MR echo signal by applying a seed-guided phase unwrapping algorithm to the image data obtained from the second MR echo signal; c) removing the effect of the background field inhomogeneties according to the unwrapped field map to yield a corrected first MR echo signal and a corrected second MR echo signal; d) calculating an intermediate data for the corrected first MR echo image according to the sequence parameters of data acquisition; e) summing an imaginary portion of the intermediate data; f) distinguishing whether a seed reference used in applying the phase unwrapping is water-dominant or fat-dominant based on the polarity of the sum of the imaginary portion of the intermediate data, and g) determining water and fat images from the corrected first and second MR echo images based on whether the seed reference is water-dominant or fat-dominant.

In a further embodiment, the invention is a method of separating and identifying water and fat magnetic resonance (MR) images using an MRI apparatus, comprising the steps of a) obtaining nuclear magnetic resonance (NMR) image data from at least a first MR echo signal and a second MR echo signal, where water and fat signals are orthogonal in the first MR echo signal and water and fat signals are either parallel or anti-parallel in the second MR echo signal; b) obtaining a field map of background main magnetic field from the second MR echo signal by applying a seed-guided phase unwrapping algorithm to the image data obtained from the second MR echo signal according to $$P = \frac{1}{2\lambda} unwrap\{\arg(S_2 \times S_2)\};$$

c) removing the effect of background field inhomogeneties according to the unwrapped field map to yield a corrected first MR echo signal and a corrected second MR echo signal;
d) calculating an intermediate data for the corrected first MR echo image according to the sequence parameters of data acquisition; e) summing the imaginary portion of the intermediate data; f) distinguishing whether a seed reference used in applying the phase unwrapping is water-dominant or fat-dominant based on the polarity of the sum of the imaginary portion of the intermediate data, and g) determining water and fat images from the corrected first and second MR echo images based on whether the seed reference is water-dominant or fat-dominant.

BRIEF DESCRIPTION OF THE DRAWINGS

The purpose and advantages gained by the present invention will be understood by careful study of the following detailed description of the presently preferred embodiment with particular reference to the accompanying drawings, of which.

DETAILED DESCRIPTION OF THE PRESENTLY PREFERRED EMBODIMENT

As is well known, nuclei precess at a particular frequency with a particular phase. By applying gradient fields to the nuclei in different orthogonal directions, the frequency and phase of the precessions can be used to spatially encode the nuclei. In one orthogonal direction, a "slice" of nuclei are excited. Within that slice, MR signals are extracted from the remaining two dimensions of the slice, using the frequency of precession of the selected nuclei to spatially encode the nuclei in one direction and using the phase of precession of the selected nuclei to spatially encode the nuclei in the second (or other) direction(s). By analyzing the complex frequency and phase of the resultant MR signal, information about the nuclei density in the selected slice can be determined.

Figure 4:
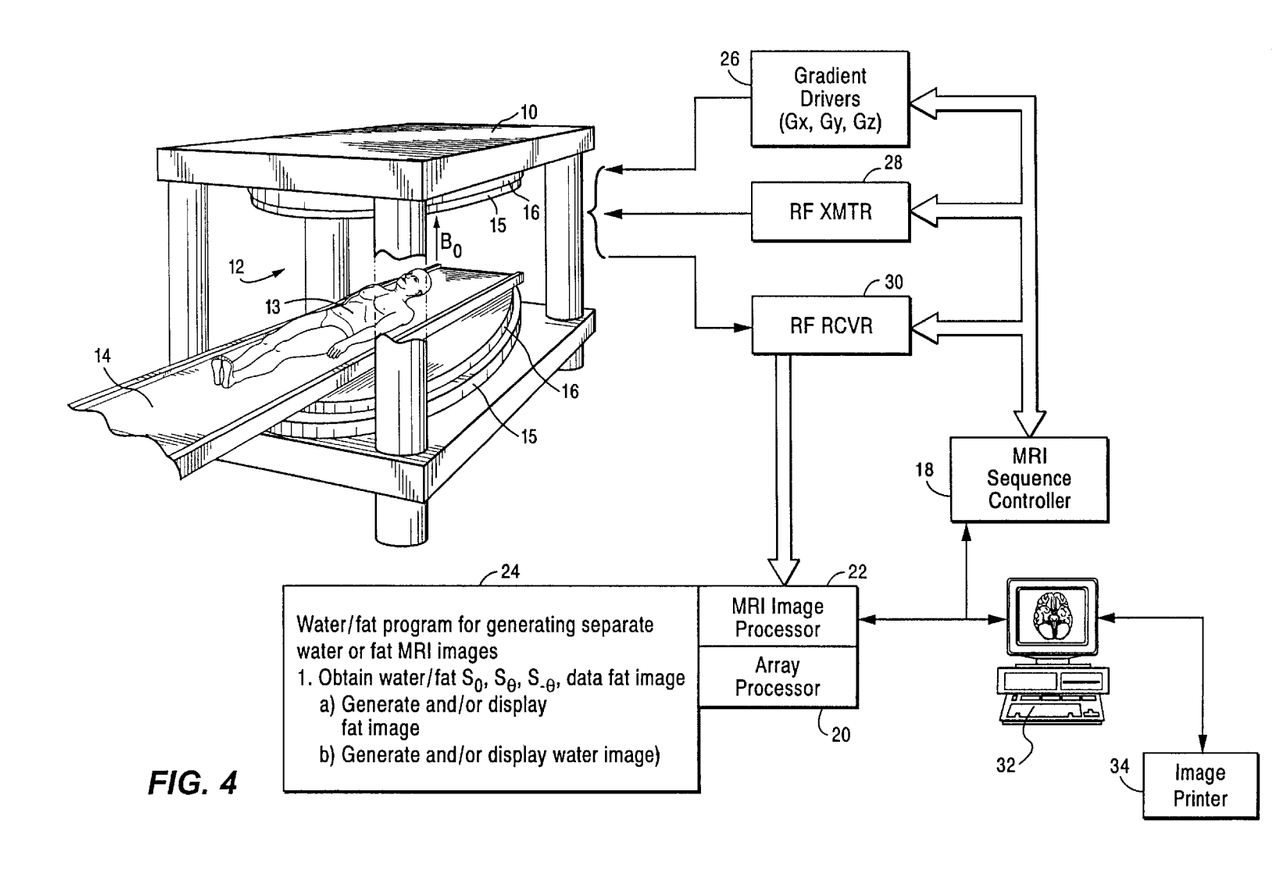
FIG. 4 is a schematic diagram of an exemplary MRI system.

FIG. 4 depicts an MRI system. One example of such a system is the Toshiba OPART™ MRI system. Such an MRI system may comprise a large polarizing magnet structure 10 which generates a substantially uniform homogeneous polarizing magnetic field $B_0$ within a patient imaging volume 12. A suitable carriage 14 inserts the desired portion of patient 13 anatomy within the image volume. Magnetic gradients are selectively created by electromagnetic gradient coils 15. RF nuclei nutation pulses are transmitted into the patient tissue within the image volume by an RF coil 16. The RF responses constituting the MR signal are received from the patient tissue via suitable RF detection coil structures 16.

To acquire MRI data, the MRI system generates magnetic gradient and RF nutation pulses via MRI pulse sequence controllers 18 under the control of a programmable computer array processor 20. The array processor and associated computer image processor 22 execute a water/fat computer software program 24. The array processor 20 and sequence controller 18 control gradient pulse amplifier drivers 26, and RF transmitter and receiver circuits 28 and 30. The MR amplifier signal receiver circuits 30 are suitably interfaced with MR signal RF coils 16 located within the shielded MRI system gantry.

The received MR responses are digitized and passed to the image processor 22 which typically includes suitable computer program storage media (not shown) wherein programs are stored and selectively utilized to control the acquisition and processing of MR signal data and to produce image displays on a CRT of control terminal 32. The control terminal may include suitable keyboard switches and the like for exerting operator control over the imaging sequence controllers 18. Images may also be recorded directly on film or on other suitable media by a printing device 34.

In conjunction with system computer/processor, an operator is typically presented on the control terminal with a menu of choices for MRI sequences and data processing techniques. One of the choices available to the MRI system operator is a program 24 for generating water/fat component images using a single-scan Three-Point Dixon MRI imaging sequence and a program for implementing a post data acquisition method of producing images. The generation of a suitable computer program or such specific instructions for system computer/image processor to effect the described process of the present invention is well within the ability of those skilled in the art in view of the particular data processing method described below and the totality of the disclosure set forth herein.

Figure 5:
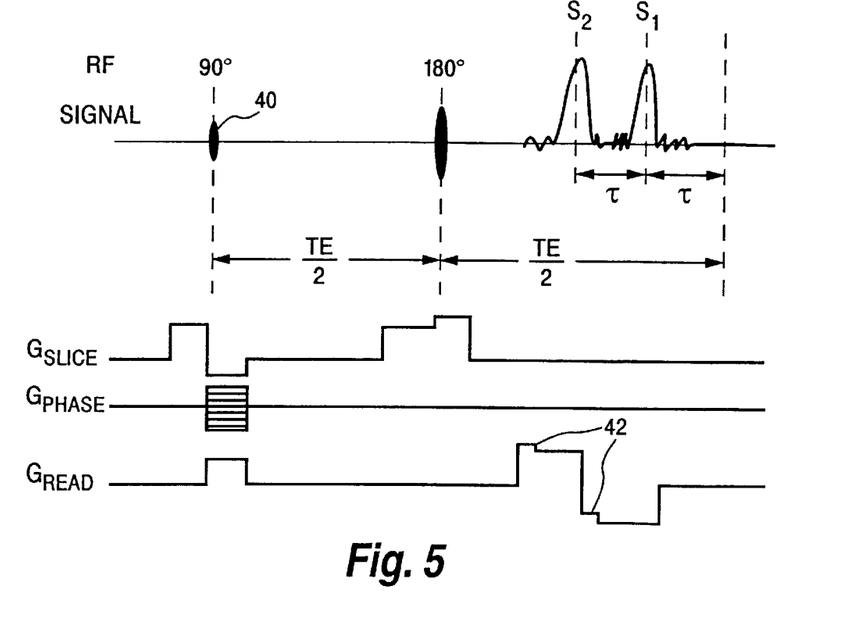
FIG. 5 is a sequence diagram of a spin-echo MR sequencing technique according to the present invention.

As shown in FIG. 5, at least two echo images, $S_1$ and $S_2$, are acquired. The acquisition of the echo images can be by multiple scans, but is preferably acquired by a single scan sequence. Acquisition sequences are controlled such that, ignoring spin relaxation, MR echo signals $S_1$ and $S_2$ can be described by:

$$S_1 = \left(W + Fe^{-i\left(\frac{1}{2}+n_1\right)\pi}\right)e^{-i\varphi}$$

$$S_2 = (W + Fe^{-in_2\pi})e^{-i\lambda\varphi}$$

where $n_1=0, \pm 1, \pm 2, \ldots$, $n_2=\pm 1, \pm 2, \pm 3, \ldots$; $\varphi$ is the $B_O$ inhomogeneity-induced phase; $\lambda=n_2/(\frac{1}{2}+n_1)$; "W" represents an echo signal from precessing water nuclei, and "F" represents an echo signal from precessing fat nuclei. Both $n_1$ and $n_2$ are sequence-controlled parameters.

A field-inhomogeneity map is determined from $S_2$ by:

$$P = \frac{1}{2\lambda} unwrap\{arg(S_2 \times S_2)\}$$

where arg( ) is an operation which yields the principal phase angle of its complex input, and "unwrap" represents algorithms for phase unwrapping to yield true phase angles from the principal values. In one preferred embodiment of the present invention, phase unwrapping is performed by the seed-oriented region-growing algorithm guided by a polynomial model, as is described in the '119 patent. Yet, in another embodiment, the background main magnetic field is represented and measured by a set of spherical harmonics. The measured coefficient of the spherical harmonics are stored and recalled to replace the polynomial model for guiding the seed-oriented region-growing algorithm of phase-unwrapping.

The field inhomogeneity phase is then removed from the echo signals $S_1$ and $S_2$ to generate $S_1'$ and $S_2'$, where:

$$S_1' = S_1 e^{iP}$$

$$S_2' = S_2 e^{i\lambda P}$$

Depending on which chemical component is used as the reference by the unwrapping algorithm, there are two possible cases (Case 1 and Case 2) of spin echo images ($S_1'$, $S_2'$) after eliminating the field inhomogeneity phase:

Case 1 (when the reference is water-dominant):

$$P = \varphi$$

$$S_1' = W + F e^{-i(\frac{1}{2}+n_1)\pi}$$

$$S_2' = W + F e^{-in_2\pi}$$

Case 2 (when the reference is fat-dominant):

$$P = \varphi\left(n_1 + \frac{1}{2}\right)\pi$$

$$S_1' = W e^{i(\frac{1}{2}+n_1)\pi} + F$$

$$S_2' = W e^{in_2\pi} + F$$

In order to distinguish the two cases above, an intermediate matrix of complex data is calculated according to $$S_1'' = R(S_1') + iI(S_1')(-1)^{n_1}$$

where R( ) and I( ) return the real part and imaginary part of the complex input, respectively; and "i" has its ordinary meaning of denoting the imaginary portion of a complex number.

Figure 6:
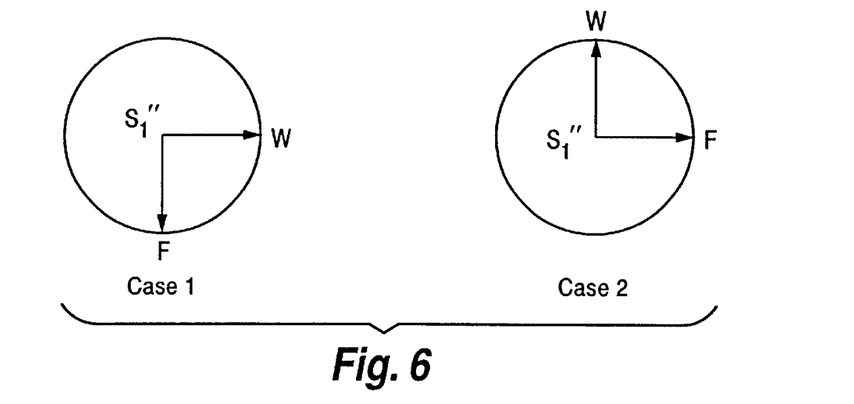
FIG. 6 is a schematic diagram in a rotating frame of intermediate data, $S_1''$, that is needed to distinguish the two cases of phase unwrapping.

As shown in FIG. 6, $S_1''$ is distinctively different between the two cases: case 1 with water-dominant reference and case 2 with fat-dominant reference. While the imaginary portion of $S_1''$ is significantly negative for case 1, that for case 2 is significantly positive. By summing the imaginary portion of $S_1''$, case 1 and case 2 can be distinguished by examining the polarity of the sum as follows:

$$Sum = \sum_{image} I(S_1'')$$

if the sum <<0, then case 1 (water-dominate) is present, and if sum >>0, then case 2 (fat-dominate) is present.

Once the echo signals $S_1'$ and $S_2'$ have been obtained, and case assignment is made between case 1 and case 2, the water and fat images are constructed from the following equations:

Case 1 (when the reference is water-dominant):

$$I_W = \frac{1}{2}|R(S_1') + I(S_1')(-1)^{(n_2-n_1)} + S_2'|$$

$$I_F = \frac{1}{2}|R(S_1') + I(S_1')(-1)^{n_1+1}(2+(-1)^{n_2}) - S_2'|$$

Case 2 (when the reference is fat-dominant):

$$I_W = \frac{1}{2}|R(S_1') + I(S_1')(-1)^{n_1}(2+(-1)^{n_2}) - S_2'|$$

$$I_F = \frac{1}{2}|R(S_1') + I(S_1')(-1)^{(n_2-n_1+1)} + S_2'|$$

Figure 7:
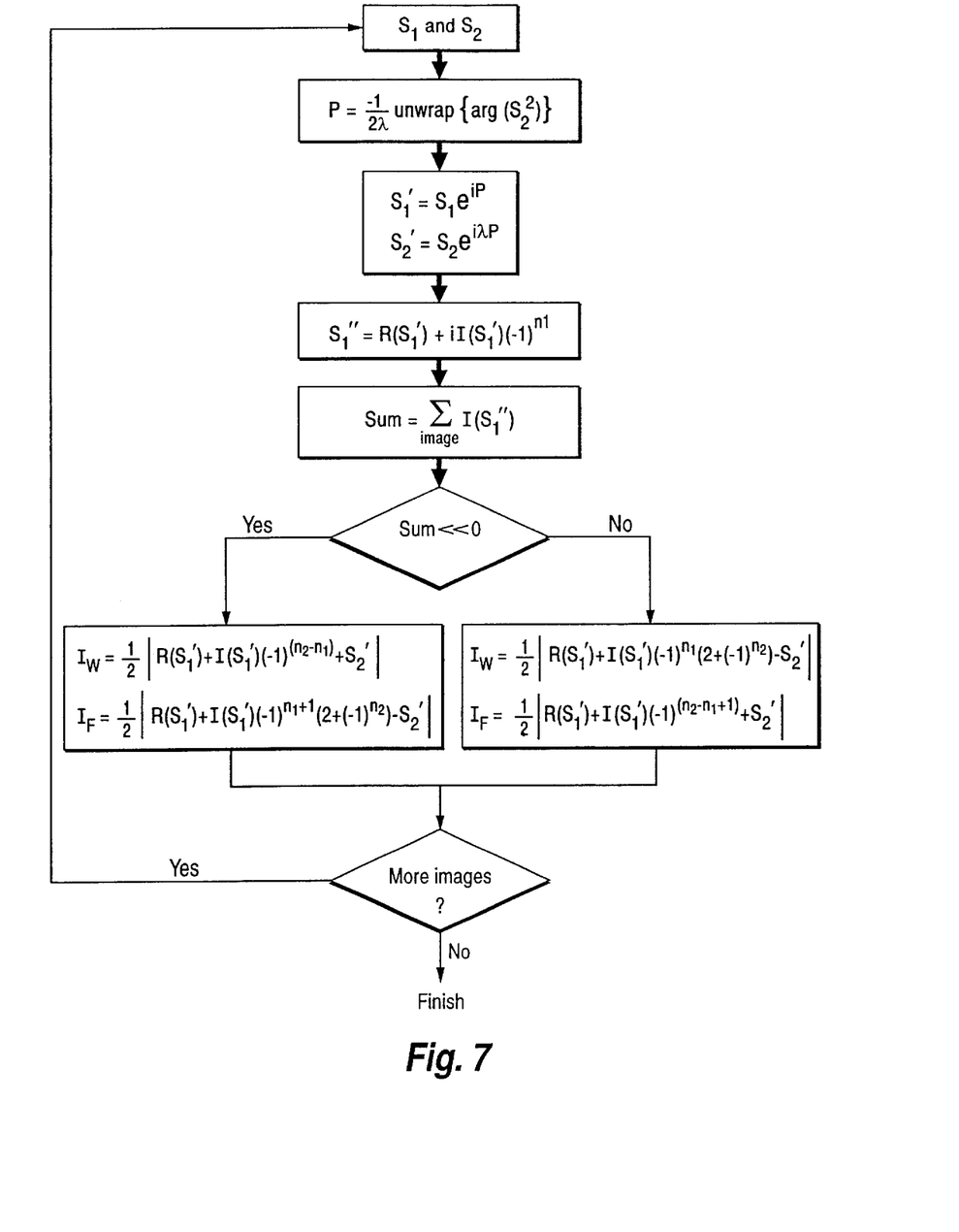
FIG. 7 is a flowchart of the data processing procedures for separating and identifying water and fat MR images according to the present invention.

A complete data processing procedure for separating and identifying water and fat images is summarized schematically in the flowchart shown in FIG. 7.

Figure 8:
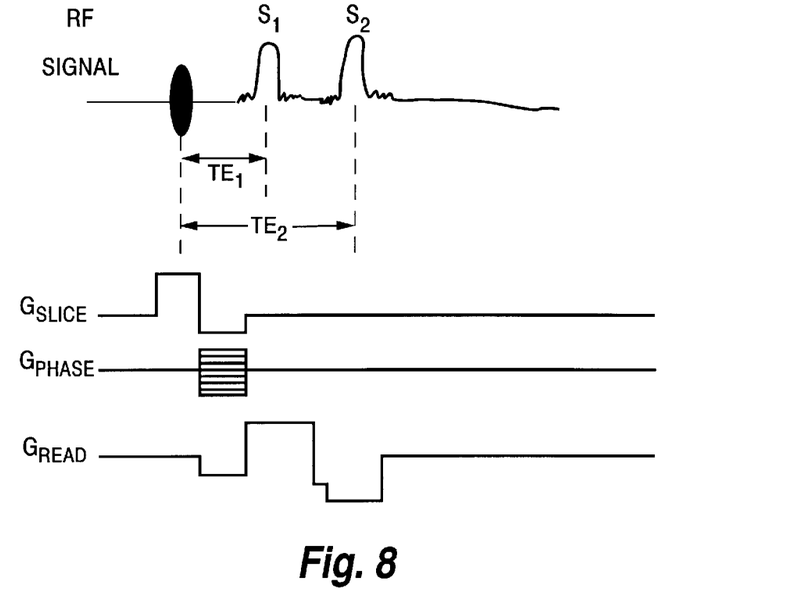
FIGS. 8 and 9 are sequence diagrams of field-echo MR sequencing techniques according to the present invention, for both 2D (FIG. 8) and 3D (FIG. 9) data acquisition.
Figure 9:
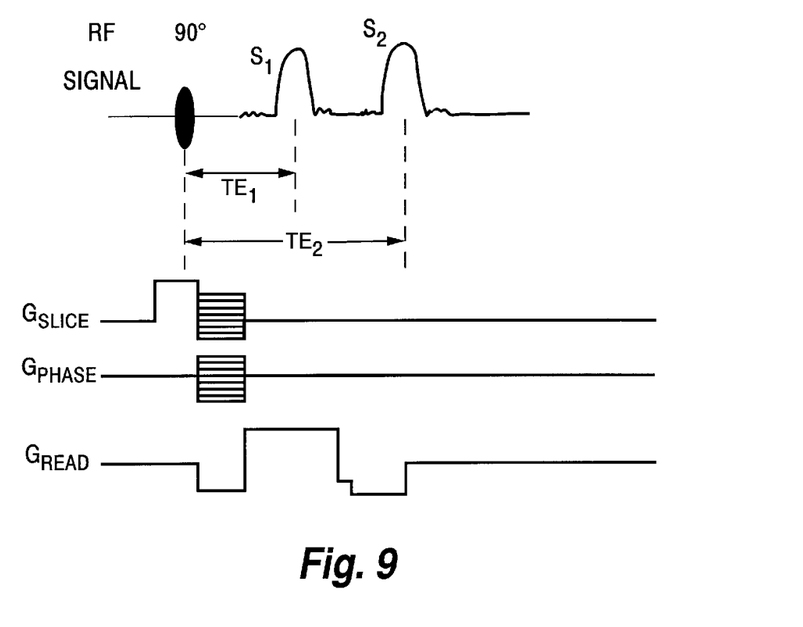

One implementation of the above-described method of data acquisition is a field-echo sequence which acquires two echo images with $n_1=0$ and $n_2=1$, such that $\lambda=2$. At 0.35 Tesla, then $TE_1=4.75$ ms and $TE_2=9.50$ ms for water and fat separation. The sequence can be used in either two-dimensional (2D) or three-dimensional (3D) imaging modes. FIGS. 8 and 9 are diagrams of the pulse sequencer for such 2D and 3D data acquisition.

Referring to FIG. 6, a spin-echo imaging sequence of the present invention basically consists of an RF nuclei nutation ("excitation") pulse, 40, accompanied by the generation of a slice selection gradient pulse, $G_{slice}$, and a phase encoding gradient pulse, $G_{pe}$, followed by three appropriately timed read-out gradient pulses, $G_{read}$, 42, which result in the acquisition of a pair of spin-echoes, $S_1$ and $S_2$.

One of such implementations is a two-echo spin-echo sequence for acquiring spin echoes $S_1$ and $S_2$ with $n_1=-1$, $n_2=-1$, and $\lambda=2$. $S_1$ and $S_2$ are acquired ahead in time from the true spin-echo position by $\tau$ and $2\tau$, respectively. At 0.35 Tesla, $\tau=4.75$ ms and thus $\lambda=2$.

Other MRI pulse sequences can be used for acquisition of the echo signals according to the present invention. One of such sequences is the echo-planar or echo-volume imaging (EPI) sequence. The EPI echo signals can be split to two groups to correspond to $S_1$ and $S_2$ according to the present invention. Yet another sequence is the fast spin-echo (FSE) sequence where two echo signals corresponding to $S_1$ and $S_2$ according to the present invention can be acquired for each RF-refocusing pulse.

While the invention has been described in connection with what is presently considered to be the most practical and preferred embodiment, it is to be understood that the invention is not to be limited to the disclosed embodiment, but on the contrary, is intended without further analysis, to so fully reveal the gist of the present invention that others can, by applying contemporary knowledge, readily adapt it for various applications without omitting features that, from the standpoint of prior art, fairly constitute essential characteristics of the generic and specific aspects of the instant contribution to the art and, therefore, such adaptations should and are intended to be comprehended within the meaning and range of equivalence of the appended claims.

What is claimed is:

1. A method of separating and identifying water and fat magnetic resonance (MR) images using an MRL apparatus, comprising:

a) obtaining nuclear magnetic resonance (NMR) image data from at least a first MR echo signal ($S_1$) and a second MR echo signal ($S_2$), where water and fat signals are orthogonal in the first MR echo signal and water and fat signals are either parallel or anti-parallel in the second MR echo signal;

b) obtaining a field map of background main magnetic field (P) from the second MR echo signal by applying a seed-guided phase unwrapping algorithm to the image data obtained from the second MR echo signal according to $$P = \frac{1}{2\lambda} unwrap\{\arg(S_2 \times S_2)\};$$

c) removing the effect of background field inhomogeneties according to the unwrapped field map to yield a corrected first MR echo signal ($S_1'$) and a corrected second MR echo signal ($S_2'$);

d) calculating an intermediate data for the corrected first MR echo signal according to sequence parameters of data acquisition;

e) summing an imaginary portion of the intermediate data;

f) distinguishing whether a seed reference used in applying the phase unwrapping is water-dominant or fat-dominant based on the polarity of the sum of the imaginary portion of the intermediate data, and g) determining water and fat images from the corrected first and second MR echo images based on whether the seed reference is water-dominant or fat-dominant.

2. The method of claim 1 wherein the first MR echo signal is determined according to: $S_1' = S_1 e^{iP}$ and the corrected second MR echo signal is determined according to $S_2' = S_2 e^{i\lambda P}$.

3. The method of claim 1 wherein the intermediate data is an intermediate matrix of complex data.

4. The method of claim 3 wherein the intermediate matrix of complex data ($S_1''$) is determined according to the following algorithm:

$$S_1'' = R(S_1') + iI(S_1')(-1)^{n_1}$$

where $n_1$ is an integer number determined by a timing sequence.

5. A method as in claim 1 wherein, if the seed reference is fat dominate, the water image ($I_w$) is determined according to the following algorithm:

$$I_w = \frac{1}{2}|R(S_1') + I(S_1')(-1)^{n_1}(2 + (-1)^{n_2}) - S_2'|$$

where $n_1$ and $n_2$ are each integers determined by a timing sequence, and the fat image ($I_F$) is determined according to the following algorithm:

$$I_F = \frac{1}{2}|R(S_1') + I(S_1')(-1)^{(n_2-n_1+1)} + S_2'|.$$

6. A method as in claim 5, wherein the sum of the imaginary portion of the imaginary portion of the intermediate data is greater than zero.

7. A method as in claim 1 wherein, if the seed reference is water dominate, the water image ($I_w$) is determined according to the following algorithm:

$$I_w = \frac{1}{2}|R(S_1') + I(S_1')(-1)^{(n_2-n_1)} + S_2'|$$

where $n_1$ and $n_2$ are integers determined by a timing sequence, and the fat image ($I_F$) is determined according to the following algorithm:

$$I_F = \frac{1}{2}|R(S_1') + I(S_1')(-1)^{n_1+1}(2 + (-1)^{n_2}) - S_2'|.$$

8. A method as in claim 7, wherein the sum of the imaginary portion is less than zero.

9. A method as in claim 1 wherein the water and fat signals are ninety degrees out of phase in the first MR echo signal, and are in-phase or one hundred and eighty degrees out-of-phase in the second MR echo signal.

10. A method as in claim 1 wherein the method steps are repeated for a plurality of first and second MR echo signals.

11. A method as in claim 1 wherein the first MR echo signal and the second MR echo signal are obtained from an echo-planar or echo-volume imaging MR pulse sequence.

12. A method as in claim 1 wherein the first MR echo signal and the second MR echo signal are obtained from a fast spin-echo MR pulse sequence.

13. A method as in claim 1 wherein the first MR echo signal and the second MR echo signal are obtained from a field-echo MR pulse sequence.

14. A method as in claim 1 wherein the first MR echo signal and the second MR echo signal are obtained from a spin-echo MR pulse sequence.

15. A method to identify water and fat magnetic resonance images comprising:

a) obtaining nuclear magnetic resonance image data from a first MR echo signal ($S_1$) and a second MR echo signal ($S_2$), where water and fat signals are orthogonal in the first MR echo signal, and water and fat signals are parallel or anti-parallel in the second MR echo signal;

b) generating a corrected first MR echo signal ($S_1'$) and a corrected second MR echo signal ($S_2'$) by applying a phase unwrapping algorithm to correct for background magnetic field inhomogeneties c) determining an intermediate matrix of complex data for the corrected first MR echo signal based on a group of corrected echo signals consisting of $S_1'$ and $S_2'$;

d) distinguishing whether a reference used in the phase-unwrapping algorithm is water-dominant or fat-dominant according to the intermediate matrix of complex data; and e) generating water images and fat images from the corrected first and second MR echo signals knowing whether the reference is water dominant or fat-dominant.

16. The method to identify water and fat magnetic resonance images comprising:
   a) obtaining nuclear magnetic resonance image data from a first MR echo signal ($S_1$) and a second MR echo signal ($S_2$), where water and fat signals are orthogonal in the first MR echo signal, and water and fat signals are parallel or anti-parallel in the second MR echo signal;
   b) generating a corrected first MR echo signal ($S_1'$) and a corrected second MR echo signal ($S_2'$) by applying a phase unwrapping algorithm to correct for background magnetic field inhomogeneties;
   c) determining an intermediate matrix of complex data for the corrected first MR echo signal;
   d) distinguishing whether a reference used in the phase-unwrapping algorithm is water-dominant or fat-dominant according to the intermediate matrix of complex data;
   e) generating water images and fat images from the corrected first and second MR echo signals knowing whether the reference is water dominant or fat-dominant, and
   wherein the intermediate matrix ($S_1''$) of complex data is determined according to the following algorithm:

$$S_1'' R(S_1')iI(S_1')(-1)^{n_1}$$

where $n_1$ is an integer number determined by a timing sequence.

17. A method to identify water and fat magnetic resonance images comprising:
   a) obtaining nuclear magnetic resonance image data from a first MR echo signal ($S_1$) and a second MR echo signal ($S_2$), where water and fat signals are orthogonal in the first MR echo signal, and water and fat signals are parallel or anti-parallel in the second MR echo signal;
   b) generating a corrected first MR echo signal ($S_1'$) and a corrected second MR echo signal ($S_2'$) by applying a phase unwrapping algorithm to correct for background magnetic field inhomogeneties;
   c) determining an intermediate matrix of complex data for the corrected first MR echo signal;
   d) distinguishing whether a reference used in the phase-unwrapping algorithm is water-dominant or fat-dominant according to the intermediate matrix of complex data;
   e) generating water images and fat images from the corrected first and second MR echo signals knowing whether the reference is water dominant or fat-dominant, and
   wherein, if the seed reference is fat dominate, the water image ($I_w$) is determined according to the following algorithm:

$$I_W = \frac{1}{2}|R(S_1') + I(S_1')(-1)^{n_1}(2 + (-1)^{n_2}) - S_2'|$$

where $n_1$ and $n_2$ are integers determined by a timing sequence, and the fat image ($I_F$) is determined according to the following algorithm:

$$I_F = \frac{1}{2}|R(S_1') + I(S_1')(-1)^{(n_2-n_1+1)} + S_2'|.$$

18. A method as in claim 17, wherein a sum of the imaginary portion of the intermediate data is greater than zero.

19. A method to identify water and fat magnetic resonance images comprising:
   a) obtaining nuclear magnetic resonance image data from a first MR echo signal ($S_1$) and a second MR echo signal ($S_2$), where water and fat signals are orthogonal in the first MR echo signal, and water and fat signals are parallel or anti-parallel in the second MR echo signal;
   b) generating a corrected first MR echo signal ($S_1'$) and a corrected second MR echo signal ($S_2'$) by applying a phase unwrapping algorithm to correct for background magnetic field inhomogeneties;
   c) determining an intermediate matrix of complex data for the corrected first MR echo signal;
   d) distinguishing whether a reference used in the phase-unwrapping algorithm is water-dominant or fat-dominant according to the intermediate matrix of complex data;
   e) generating water images and fat images from the corrected first and second MR echo signals knowing whether the reference is water dominant or fat-dominant, and
   wherein, if the reference is water dominate, the water image ($I_w$) is determined according to the following algorithm:

$$I_W = \frac{1}{2}|R(S_1') + I(S_1')(-1)^{(n_2-n_1)} + S_2'|$$

where $n_1$ and $n_2$ are integer numbers determined by a timing sequence, and the fat image ($I_F$) is determined according to the following algorithm:

$$I_F = \frac{1}{2}|R(S_1') + I(S_1')(-1)^{n_1+1}(2 + (-1)^{n_2}) - S_2'|.$$

20. A method as in claim 19, wherein a sum of the imaginary portion of the intermediate data is less than zero.

21. A method as in claim 15 wherein the water and fat signals are ninety degrees out of phase in the first MR echo signal, and are in-phase or one hundred and eighty degrees out of phase in the second MR echo signal.

22. A method as in claim 15 wherein the method steps are repeated for a plurality of first and second MR echo signals.

23. A method as in claim 15 wherein the first MR echo signal and the second MR echo signal are obtained from an echo-planar or echo-volume imaging MR pulse sequence.

24. A method as in claim 15 wherein the first MR echo signal ($S_1$) and the second MR echo signal ($S_2$) are obtained from a fast spin-echo MR pulse sequence.

25. A method as in claim 15 wherein the first MR echo signal and the second MR echo signal are obtained from a field-echo MR pulse sequence.

26. A method as in claim 15 wherein the first MR echo signal and the second MR echo signal are obtained from a spin-echo MR pulse sequence.

27. A method of separating and identifying water and fat magnetic resonance (MR) images using an MRI apparatus, comprising:
   a) obtaining nuclear magnetic resonance (NMR) image data from at least a first MR echo signal and a second MR echo signal, where water and fat signals are orthogonal in the first MR echo signal and water and fat signals are either parallel or anti-parallel in the second MR echo signal;
   b) obtaining a field map of background main magnetic field from the second MR echo signal by applying a seed-guided phase unwrapping algorithm to the image data obtained from the second MR echo signal;

c) removing an effect of the background field inhomogeneties according to the field map to yield a corrected first MR echo signal and a corrected second MR echo signal;

d) calculating an intermediate data for the corrected first MR echo image according to sequence parameters of data acquisition;

e) summing an imaginary portion of the intermediate data;

f) distinguishing whether a seed reference used in applying the phase unwrapping is water-dominant or fat-dominant based on a polarity of the sum of the imaginary portion of the intermediate data, and g) determining water and fat images based on a group of corrected MR echo images consisting of the corrected first and second MR echo images, and based on whether the seed reference is water-dominant or fat-dominant.

28. A method of separating and identifying water and fat magnetic resonance (MR) images using an MRI apparatus, comprising:

a) obtaining nuclear magnetic resonance (NMR) image data from at least a first MR echo signal ($S_1$) and a second MR echo signal ($S_2$), where water and fat signals are orthogonal in the first MR echo signal and water and fat signals are either parallel or anti-parallel in the second MR echo signal, and the echo signals are defined as follows:

$$S_1 = \left(W + Fe^{-i\left(\frac{1}{2}+n_1\right)\pi}\right)e^{-i\varphi}, \text{ and}$$

$$S_2 = (W + Fe^{-in_2\pi})e^{-i\lambda\varphi}$$

where W represents an echo signal from precessing water nuclei, F represents an echo signal from precessing fat nuclei, $n_1$ and $n_2$ are integer numbers determined by a timing sequence; $\varphi$ is a static magnetic field ($B_O$) inhomogeneity-induced phase; and $\lambda$ is equal to $n_2/(\frac{1}{2}+n_1)$;

b) obtaining a field map of background main magnetic field (P) from the second MR echo signal by applying a seed-guided phase unwrapping algorithm to the image data obtained from the second MR echo signal according to $$P = \frac{1}{2\lambda} unwrap\{\arg(S_2 \times S_2)\},$$

where arg() is an operation which yields a principal phase angle of a complex input, and unwrap represents algorithms for phase unwrapping to yield true phase angles from the principal values;

c) removing the effect of background field inhomogeneties according to the unwrapped field map to yield a corrected first MR echo signal ($S_1'$) and a corrected second MR echo signal ($S_2'$);

d) calculating an intermediate data for the corrected first MR echo signal according to sequence parameters of data acquisition;

e) summing an imaginary portion of the intermediate data;

f) distinguishing whether a seed reference used in applying the phase unwrapping is water-dominant or fat-dominant based on the polarity of the sum of the imaginary portion of the intermediate data, and g) determining water and fat images from the corrected first and second MR echo images based on whether the seed reference is water-dominant or fat-dominant.

* * * * *

UNITED STATES PATENT AND TRADEMARK OFFICE
CERTIFICATE OF CORRECTION

PATENT NO. : 6,603,990 B2  Page 1 of 1
APPLICATION NO. : 09/925520
DATED : August 5, 2003
INVENTOR(S) : Zhang et al.

It is certified that error appears in the above-identified patent and that said Letters Patent is hereby corrected as shown below:

Claim 1, column 11, line 8, change "MRL" to --MRI--

Claim 6, column 12, line 7, (second occurrence) delete "of the imaginary portion"

Signed and Sealed this

Twelfth Day of August, 2008

JON W. DUDAS
*Director of the United States Patent and Trademark Office*